United States Patent [19]

Briggs et al.

[11] Patent Number: 4,564,715

[45] Date of Patent: Jan. 14, 1986

[54] PREPARATION OF MONOALKYLENE GLYCOLS IN TWO STAGES

[75] Inventors: John R. Briggs; George L. O'Connor; John H. Robson, all of Charleston, W. Va.

[73] Assignee: Union Carbide Corporation, Danbury, Conn.

[21] Appl. No.: 663,828

[22] Filed: Oct. 23, 1984

Related U.S. Application Data

[63] Continuation of Ser. No. 594,256, Mar. 28, 1984, abandoned.

[51] Int. Cl.[4] ...................... C07C 31/20; C07C 33/26; C07C 35/14; C07C 33/035
[52] U.S. Cl. .................................... 568/867; 568/811; 568/833; 568/857
[58] Field of Search ................ 568/867, 833, 811, 857

[56] References Cited

U.S. PATENT DOCUMENTS 2,409,441 10/1946 Metzger .............................. 568/867
2,615,901 10/1952 McClellan .......................... 568/867

FOREIGN PATENT DOCUMENTS 73035 6/1981 Japan .................................. 568/867

*Primary Examiner*—J. E. Evans
*Attorney, Agent, or Firm*—Norman L. Balmer

[57] ABSTRACT

High selectivity of monoalkylene glycol is obtained by contacting in an associated moiety-forming zone alkylene oxide and a selectivity enhancing, dissociatable metalate anion under conditions sufficient to associate at least a portion of the alkylene oxide with metalate anion, and then contacting the associated moiety with water in a glycol-forming zone to form alkylene glycol. The alkylene glycol can be separated from metalate anion. Desirably, the metalate anion can be recycled to the associated moiety-forming zone.

22 Claims, No Drawings

PREPARATION OF MONOALKYLENE GLYCOLS IN TWO STAGES

This application is a continuation, of application Ser. No. 594,256, filed Mar. 28, 1984, now abandoned.

This invention relates to processes for the preparation of monoalkylene glycols from alkylene oxides and water involving the use of selectivity-enhancing, dissociatable metalate anion-containing material. The processes of this invention enable the production of monoalkylene glycols with high selectivity by sequentially contacting the alkylene oxide with metalate anion and then with water.

Introduction to Alkylene Glycols

Commercial processes for the preparation of alkylene glycols, for example, ethylene glycol, propylene glycol and butylene glycol, involve the liquid-phase hydration of the corresponding alkylene oxide in the presence of a large molar excess of water (see, for example, Kirk-Othmer, *Encyclopedia of Chemical Technology*, Vol. 11, Third Edition, page 939 (1980)). The hydrolysis reaction is typically conducted at moderate temperatures, e.g., about 100° C. to about 200° C., with water being provided to the reaction zone in excess of 15 moles per mole of alkylene oxide. The primary by-products of the hydrolysis reaction are di- and polyglycols, e.g., dialkylene glycol, trialkylene glycol and tetra-alkylene glycol. The formation of the di- and polyglycols is believed to be primarily due to the reaction of alkylene oxide with alkylene glycol. As alkylene oxides are generally more reactive with alkylene glycols than they are with water, the large excesses of water are employed in order to favor the reaction with water and thereby obtain a commercially attractive selectivity to the monoglycol product.

Since the alkylene glycols must be recovered from the hydrolysis reaction mixtures, the large excess of water can result in an energy intensive procedure. Typically, the water is removed by evaporation to leave an alkylene glycol-containing residue which is purified by distillation. Hence, a reduction in the amount of water employed while maintaining, or enhancing, selectivity toward the monoglycol product could be beneficial from the standpoint of energy efficiency.

The hydrolysis reaction proceeds uncatalyzed; however, the presence of acids or bases enhances the rate of reaction. Acid and base catalysts, however, do have shortcomings. For instance, base catalysts are generally not selective to the formation of the monoglycol product and acid catalysts are typically associated with corrosion problems. Hence, commercial processes typically utilize relatively neutral hydrolysis conditions (for instance, pH 6-10).

Representative of the numerous acid catalysts that have been suggested for use in the hydration of alkylene oxides include fluorinated alkyl sulfonic acid ion exchange resins (U.S. Pat. No. 4,165,440, issued Aug. 21, 1979); carboxylic acids and halogen acids (U.S. Pat. No. 4,112,054, issued Sept. 5, 1978); strong acid cation exchange resins (U.S. Pat. No. 4,107,221, issued Aug. 15, 1978); aliphatic mono- and/or polycarboxylic acids (U.S. Pat. No. 3,933,923, issued Jan. 20, 1976); cationic exchange resins (U.S. Pat. No. 3,062,889, issued Nov. 6, 1962); acidic zeolites (U.S. Pat. No. 3,028,434, issued Apr. 3, 1962); sulfur dioxide (U.S. Pat. No. 2,807,651, issued Sept. 24, 1957); trihalogen acetic acids (U.S. Pat. No. 2,472,417, issued June 7, 1949); and copper-promoted aluminum phosphate (U.S. Pat. No. 4,014,945, issued Mar. 29, 1977).

In addition to the acid catalysts, numerous catalysts have been suggested for the hydration of alkylene oxides in the presence of carbon dioxide. These include alkali metal halides, such as chlorides, bromides and iodides; quaternary ammonium halides such as tetramethyl ammonium iodide and tetramethyl ammonium bromide (British Pat. No. 1,177,877); organic tertiary amines such as triethylamine and pyridine (German published patent application 2,615,595, Oct. 14, 1976, and U.S. Pat. No. 4,307,256, issued Dec. 22, 1981); quaternary phosphonium salts (U.S. Pat. No. 4,160,116, issued July 3, 1979); chlorine or iodine-type anion exchange resins (Japanese Kokai No. 57/139,026, published Aug. 27, 1982); and partially amine-neutralized sulfonic acid catalyst, e.g., partially amine-neutralized sulfonic acid resin (U.S. Pat. No. 4,393,254, issued July 12, 1983).

Various metal-containing compounds, including metal oxides, have been proposed as catalysts for the hydrolysis of alkylene oxides. For example, U.S. Pat. No. 2,141,443, issued Dec. 27, 1938, discloses the production of glycols by the reaction of alkylene oxide with water in the presence of a dehydrating metal oxide, for example, alumina, thoria, or oxides of tungsten, titanium, vanadium, molybdenum or zirconium. The reaction is carried out in the liquid phase and under conditions of temperature and pressure suited to maintain such phase. In example 7, the patentees disclose rendering a yellow tungstic acid catalyst more mechanically stable by admixture with a mixture of silicon ester, alcohol and water followed by drying the catalyst. Similarly, U.S. Pat. No. 2,807,651, issued Sept. 24, 1957, states that it is known to catalyze the reaction of an alkylene oxide and water by alkali metal bases, alcoholates, oxides of titanium, tungsten and thorium.

Many metals such as vanadium, molybdenum, tungsten, titanium, chromium, zirconium, tantalum, rhenium and niobium, have also been proposed as components for catalysts for preparing 1,2-epoxides of alpha-olefins and organic hydroperoxides and often are present during a subsequent hydrolysis reaction. For instance, Examples I and III of U.S. Pat. No. 3,475,499, issued Oct. 28, 1969, disclose that a mixture of normal alpha-olefins containing 11 to 15 carbon atoms was epoxidized with ethylbenzene hydroperoxide in the presence of molybdenum naphthanate catalyst. After distillation, the bottoms, which contained the 1,2-epoxides and the molybdenum-containing catalyst, were contacted with water containing 0.5 percent sodium hydroxide at a temperature of 90° C. That reaction product was distilled and a conversion of 1,2-epoxides was reported to be 100 percent and the selectivity to 1,2-glycols was reported to be 94 percent.

More recently, U.S. Pat. No. 4,277,632, issued July 7, 1981, discloses a process for the production of alkylene glycols by the hydrolysis of alkylene oxides in the presence of a catalyst of at least one member selected from the group consisting of molybdenum and tungsten. The patent discloses that the catalyst may be metallic molybdenum or metallic tungsten, or inorganic or organic compounds thereof, such as oxides, acids, halides, phosphorous compounds, polyacids, alkali metal and alkaline earth metal salts, ammonium salts and heavy metal salts of acids and polyacids, and organic acid salts. An objective of the disclosed process is stated to be the hydrolysis of alkylene oxides wherein water is present in about one to five times the stoichiometric value without forming appreciable amounts of by-products such as the polyglycols. The reaction may be carried out in the presence of carbon dioxide; however, when the reaction is carried out in the presence of nitrogen, air, etc., the patentees state that the pH of the reaction mixture should be adjusted to a value in the range of 5 to 10. Japanese Kokai No. JA 54/128,507, published Oct. 5, 1979, discloses a process for the production of alkylene glycols from alkylene oxides and water using metallic tungsten and/or tungsten compounds.

Japanese Kokai No. JA 56/073,035, published June 17, 1981, discloses a process for the hydrolysis of alkylene oxide under a carbon dioxide atmosphere in the presence of a catalyst consisting of a compound containing at least one element selected from the group of titanium, zirconium, vanadium, niobium, tantalum and chromium. The compounds include the oxides, sulfides, acids, halides, phosphorous compounds, polyacids, alkali metal salts of acids and polyacids, ammonium salts of acids and polyacids, and heavy metal salts of acids.

Japanese Kokai No. JA 56/073,036, published June 17, 1981, discloses a process for the hydrolysis of alkylene oxide under a carbon dioxide atmosphere in the presence of a catalyst consisting of a compound containing at least one element selected from a group comprising aluminum, silicon, germanium, tin, lead, iron, cobalt and nickel.

Japanese Kokai No. JA 56/92228, published July 25, 1981, is directed to processes for producing highly pure alkylene glycols. The disclosure is directed to a distillation procedure for recovery of a molybdenum and/or tungsten-containing catalyst from an alkylene oxide hydrolysis process in the presence of carbon dioxide. The application states that the catalyst is at least one compound selected from the group consisting of compounds of molybdenum and tungsten which compound may be in combination with at least one additive selected from the group consisting of compounds of alkali metals, compounds of alkaline earth metals, quaternary ammonium salts and quaternary phosphonium salts. The preferred catalysts are stated to be molybdic acid, sodium molybdate, potassium molybdate, tungstic acid, sodium tungstate and potassium tungstate. Potassium iodide is the only additive employed in the examples.

U.S. patent application Ser. Nos. 428,815, filed Sept. 30, 1982, (now abandoned) and 530,235, filed Sept. 8, 1983, of J. H. Robson and G. E. Keller, disclose the production of monoalkylene glycols with high selectivity by the reaction of a vicinal alkylene oxide with water in the presence of a water-soluble vanadate. Hence, lower water to alkylene oxide ratios can be employed using the disclosed process with attractive selectivities to the monoglycol products. The counter ion to the vanadate is selected to provide a water-soluble vanadate salt under the reaction conditions employed and alkali metals, alkaline earth metals, quaternary ammonium, ammonium, copper, zinc, and iron are suggested cations. It is also disclosed that the vanadate may be introduced into the reaction system in the salt form or on a support such as silica, alumina, zeolites and clay. Since the vanadate ion is water-soluble, it can be lost from the reaction system and means must be provided to recover it from the effluent from the reaction zone.

Overview of the Invention

The processes of this invention relate to making alkylene glycols comprising contacting in an associated moiety-forming zone alkylene oxide with selectivity enhancing, dissociatable metalate anion-containing material under conditions sufficient to associate at least a portion of the alkylene oxide with the metalate anion to provide an associated moiety. The contacting of the alkylene oxide and metalate anion is conducted in the substantial absence of polyglycol-forming amounts of water, that is, any water present is in an amount insufficient to form significant amounts of dialkylene glycols and polyalkylene glycols. Hence, although substantially anhydrous conditions may exist, the presence of some water is not precluded. The associated moiety is then contacted in a glycol-forming zone with water under conditions sufficient to form alkylene glycol. The alkylene glycol can then be separated from the metalate anion which, if desired, can be reused in the process.

By the process of this invention, it is possible to produce monoalkylene glycol with very high selectivity, even essentially 100 percent selectivity, to the monoalkylene glycol product. Thus, when dialkylene glycols and polyalkylene glycols are not sought as by-products, the processes of this invention enable the production of the monoalkylene glycol product to the substantial exclusion of the production of higher glycols. Hence, not only can the desired product, monoalkylene glycol, be obtained in greater amounts per unit amount of alkylene oxide, but the capital and energy costs to separate the higher glycols from monoalkylene glycol may even be avoided.

Alternatively, processes of this invention can be operated to produce small, but controlled, amounts of dialkylene glycol or higher polyalkylene glycols. This aspect of the invention may be particularly attractive when some dialkylene glycol is desired, but operations under conventional hydrolysis conditions would yield amounts of dialkylene glycol in excess of that which is sought.

The processes of this invention also offer additional design flexibility for integrated hydrolysis operations. For example, the formation of the associated moiety from the alkylene oxide and the metalate anion is exothermic as is the hydrolysis of alkylene oxide. The extent of heat production in each stage can be varied by varying the amount of metalate anion in the first stage. At one extreme, sufficient metalate anion and adequate process conditions are used to substantially completely convert the alkylene oxide to the associated moiety in the first stage. Relatively little heat generation would exist in respect to the second stage. In another case, only a portion of the alkylene oxide is converted to the associated moiety in the first stage, and greater heat production occurs in the second stage.

Discussion Relating to the Reactants

Alkylene oxides which may be used to produce alkylene glycols in the processes of this invention are vicinal alkylene oxides having the general formula:

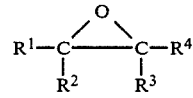

wherein $R^1$, $R^2$, $R^3$ and $R^4$ are the same or different and are hydrogen or hydrocarbyl-containing substituents of 1 to about 20 carbon atoms. Often $R^1$, $R^2$, $R^3$ and $R^4$ are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms. Representative of alkylene oxides are ethylene oxide, propylene oxide, butylene oxide, including isobutylene oxide, 1,2-butylene oxide and 2,3-butylene oxide, pentylene oxide, styrene oxide, cyclohexene oxide and the like. Preferably, the alkylene oxide is an aliphatic alkylene oxide having 2 or 3 carbon atoms, i.e., ethylene oxide and propylene oxide.

Alkylene oxides are well known, as is their preparation. For example, alkylene oxide can be prepared by reacting an olefin with an organohydroperoxide in the presence of a catalyst or by the partial oxidation of an alkene with a molecular oxygen-containing gas in the presence of a silver catalyst.

Water (as the liquid or steam) is also employed as a reagent for the formation of the corresponding alkylene glycol. Usually the water is of sufficient purity to provide a suitable quality alkylene glycol product. Liquid water may be distilled or demineralized, for example, by ion exchange treatment.

The metalate anions are characterized by an anionic structure containing at least one metal atom and at least one oxygen ligand that is conventionally characterized as a double bonded oxygen atom.

The metalate anions which may be useful in the processes of this invention comprise a polyvalent metal having a positive functional oxidation state, e.g., of at least +3, say, +4 or +6 or +7, and may be a transition metal, and at least the oxygen ligand which is conventionally characterized as a double-bonded oxygen atom. Metalate anions may be illustrated by the following formula:

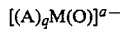

wherein a— is the negative charge of the anion which is between −1 and −4, A is one or more substituents to fill the remaining valencies (q) of M and may be the same or different and may be, for instance, double-bonded oxygen; an organic radical such as an alkyl, alkoxy, acyl, aryl, amino, phosphine, etc., usually of 1 to about 12 carbon atoms; halogen (e.g., chlorine, fluorine, iodine); —O— or —S— wherein the remaining valency of the oxygen atom is in free ionic form or is bonded to a metal atom (as in a bimetal or polymetal-containing metalate) or cation. Most commonly A is —O— or ═O. Even when the A in the starting organometalate is other than —O—, e.g., chlorine, it is possible that the original substituent becomes replaced by —O— in the course of the process.

Particularly preferred metals for the metalate anions include the metals in groups Vb and VIb of the periodic chart such as vanadium, molybdenum and tungsten, although other metals such as rhenium and germanium may also find application. Representative metalate anions which are especially useful include molybdate, tungstate, metavanadate, hydrogen pyrovanadate and pyrovanadate (although because of the complex chemistry associated with many metalate anions, the precise structure of the operative specie or species may be different). Frequently, the metalate anion comprises at least one anion conventionally characterized by the formulae $[MoO_4]^{2-}$, $[VO_3]^-$, $[V_2O_7H]^{3-}$, $[V_2O_7]^{4-}$, and $[WO_4]^{2-}$; however, it is recognized that the chemistry of these metalate anions, particularly the vanadates, is complex, and the exact chemical formula under the conditions of the process may prove to be different.

Not all metalate anions, including those of vanadium, tungsten and molybdenum, exhibit desired activity with alkylene oxide. For example, it has been observed that paramolybdate and paratungstate anions (as the metalate anion added) appear to exhibit little, if any, activity for enhancing selectivity.

Since the processes of this invention are conducted in two steps with the first step having an absence of polyglycol-forming amounts of water, and the second step involving the formation of the alkylene glycol through hydrolysis, a wider range of metalate anions are useful than would be useful if the process were conducted in one stage. For example, the conditions of the first step can be optimized for the production of the associated moiety, and those of the second stage can be optimized for the production of the alkylene glycol. Hence, even metalate anions which do not materially affect the selectivity to monoalkylene glycol in the presence of water may find application in processes in accordance with this invention.

However, in an aspect of the invention, the metal for the metalate anion is selected on the basis of the nucleophilicity and electrophilicity in the anion with respect to alkylene oxide in the environment. For example, the metal as in the metalate often has a nucleophilicity with respect to ethylene oxide greater than that exhibited by rhenium as in rhenate anion under the same conditions. Also, it is frequently the case that the metal as the metalate has an electrophilicity with respect to ethylene oxide greater than that exhibited by vanadium as in orthovanadate (as that species) under the same conditions.

A particularly convenient method for approximating nucleophilicity and electrophilicity characteristics of a metal in a metalate anion is by comparing the rate and selectivity to monoethylene glycol under substantially the same hydrolysis conditions but employing an equimolar amount (based on the anion) of the subject metalate anion and the reference anion. For the sake of ease, the cation may be sodium. If the rate and/or selectivity to the monoethylene glycol is less than that provided by rhenium as the rhenate anion, then the metal as the metalate is probably less nucleophilic than rhenium with respect to ethylene oxide. If the production of diethylene glycol and polyethylene glycol is greater than that provided with vanadium as orthovanadate, regardless of the rate of formation of ethylene glycols, then the metal as the metalate is probably less electrophilic than orthovanadate with respect to ethylene oxide.

The metalate anions are associated with a cation and are dissociatable from the cation, particularly in an aqueous medium.

The cations are substantially inert to water, alkylene oxide and alkylene glycol, and the preferred cations are those whose degradation products do not adversely affect the quality of the alkylene glycol or can facilely be removed from alkylene glycol product.

Cations to metalate anions include the alkali metal salts, quaternary ammonium salts, ammonium salts, and the like, which provide water-soluble metalates, and include cations which are substantially insoluble, or have little solubility, in water at reaction conditions providing that the metalate anion is able to become associated with, i.e., react with, the alkylene oxide. This reactivity is believed to exist when the metalate anion is capable of being dissociated from the cation. Thus, calcium vanadate, which has little solubility in water and retains the metalate anion tightly bound, has not been found to be an acceptable metalate-containing compound. On the other hand, where the cation is an essentially insoluble quaternary ammonium moiety, the dissociatable nature of the metalate anion is believed to permit its usefulness in accordance with the invention.

The organic-containing metalates (hereinafter referred to as organometalates) are generally preferred since they may be preferentially soluble in a water-immiscible organic solvent or be substantially insoluble in water so that the separation of the metalate anion-containing material from the alkylene glycol/water product can readily be effected, e.g., by extraction or phase separation.

Organometalates may be represented by the formula:

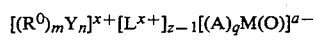

wherein $[(R^0)_m Y_n]^{x+}$ is an organic-containing cation having a positive charge of x and Y is a polyvalent element, which is an ionic charge carrying center, each $R^0$ is the same or different and is hydrogen or hydrocarbyl-containing substituent with the proviso that the organic-containing cation has at least one $R^0$ which contains a hydrocarbyl substituent, m is the average number of electron pairs shared by Y with the total $R^0$ groups, n is the number of charge carrying centers, wherein m, n and x are related by the equation x=n (V-m) in which V is the average functional oxidation state of Y wherein each electron pair used by each Y in bonding to $R^0$ is given the value of 1 and the functional oxidation state of Y is the sum of the electron pairs bonding to $R^0$ and x/n, wherein x is an integer of 1 to 2; wherein L is a cation which has a positive charge of x' and which may be the same or different from the organo-containing cation, where x' is usually 1 or 2; wherein z is the number of organo-containing cations which is from 1 to 3. Hence, the negative charge, a, of the metalate anion equals the amount of $x + [(z-1)(x')]$.

The hydrocarbyl-containing substituents useful in the organo-containing cation contain at least one carbon atom, frequently at least four carbon atoms, and may be further substituted with moieties that are not reactive with the anion.

L may be any suitable cation and often is another organic-containing cation or a non-organic-containing cation which serves to balance the charge of the anion. L may include alkali metals, alkaline earth metals, copper, zinc, iron, ammonium cations, phosphonium cations, suflonium cations, and other cations including organic-containing cations, e.g., containing alkyl, alkoxy, acyl, aryl, amino, phosphino, etc., groups of 1 to about 12 carbons.

Suitable cations may include structures represented by the formulae:

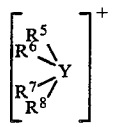

or

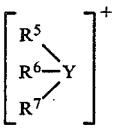

where Y is nitrogen, phosphorous, or arsenic for formula A, or sulfur for formula B, i.e., ammoniums, phosphoniums, arsoniums and sulfoniums, where each of $R^5$, $R^6$, $R^7$ and $R^8$ may be the same or different and may combine to form cyclic structures. Exemplary of each of $R^5$, $R^6$, $R^7$ and $R^8$ are hydrogen and unsubstituted and substituted hydrocarbyls of 1 or more carbon atoms, e.g., to about 70 carbon atoms. Representative cations are disclosed in copending U.S. patent application Ser. No. 594,264, filed on even date herewith, of J. R. Briggs and J. H. Robson, herein incorporated by reference.

At least one of $R^5$, $R^6$, $R^7$ and $R^8$ may be bonded or complexed to an organic or inorganic solid. For example, in copending U.S. patent application Ser. No. 594,268, filed on even date herewith, of R. D. Best, J. A. Collier, B. T. Keen, and J. H. Robson, herein incorporated by reference, anion exchange resins are disclosed which have electropositive complexing sites which, among other possibilities, can be quaternary ammonium or quaternary phosphonium moieties that are in association with the metalate anion.

Other organo-containing cations which may be useful include the bis(hydrocarbyl-phosphine)iminiums represented by the formula

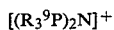

wherein each $R^9$ may be the same or different and may be the same as set forth for $R^5$ to $R^8$. Illustrative iminiums are disclosed in Ser. No. (D-13,956).

Illustrative of the organo-containing cations are tetrahydrocarbyl ammoniums, e.g., tetramethyl ammonium, tetraethyl ammonium, tetra-n-propyl ammonium, tetra-n-butyl ammonium, tetra-isobutyl ammonium, trimethyl butyl ammonium, tetraheptyl ammonium, tetraphenyl ammonium, tetrabenzyl ammonium, tetradodecyl ammonium, tetraoctadecyl ammonium, and the like; trihydrocarbyl ammonium, e.g., trimethyl ammonium, triethyl ammonium, triphenyl ammonium, tridodecyl ammonium, trioctadecyl ammonium, and the like; dihydrocarbyl ammoniums, e.g., dimethyl ammonium, diethyl ammonium, di-n-butyl ammonium, di-n-heptyl ammonium, diphenyl ammonium, dibenzyl ammonium, didodecyl ammonium, dioctacedyl ammonium, and the like; hydrocarbyl ammoniums, e.g., methyl ammonium, n-butyl ammonium, dodecyl ammonium, octadecyl ammonium, phenyl ammonium, benzyl ammonium, and the like; tetrahydrocarbyl phosphoniums, e.g., tetramethyl phosphonium, tetraethyl phosphonium, tetra-n-propyl phosphonium, tetra-n-butyl phosphonium, tetra-isobutyl phosphonium, trimethyl butyl phosphonium, tetraheptyl phosphonium, tetraphenyl phosphonium, tetrabenzyl phosphonium, tetradodecyl phosphonium, tetraoctadecyl phosphonium, and the like; trihydrocarbyl phosphonium, e.g., trimethyl phosphonium, triethyl phosphonium, triphenyl phosphonium, tridodecyl phosphonium, trioctadecyl phosphonium, and the like; dihydrocarbyl phosphoniums, e.g., dimethyl phosphonium, diethyl phosphonium, di-n-butyl phosphonium, di-n-heptyl phosphonium, diphenyl phosphonium, dibenzyl phosphonium, didodecyl phosphonium, dioctadecyl phosphonium, and the like; hydrocarbyl phosphoniums, e.g., methyl phosphonium, n-butyl phosphonium, dodecyl phosphonium, octadecyl phosphonium; phenyl phosphonium, benzyl phosphonium, and the like; bis(-hyrocarbyl phosphine)iminiums such as bis(triphenylphosphine)iminium, bis(tribenzyl-phosphine)iminum, bis(trimethyl-phosphine)iminum, bis(tridodecyl-phosphine)iminium, and the like; quaternized diamines such as N,N'-bis(trimethyl)propylene diamine, N,N'-bis(triphenyl)propylene diamine, N,N'-bis(trioctadecyl)propylene diamine; and quaternized diphosphines such as P,P'-bis(trimethyl)propylene diphosphine, and the like.

The metalate anion may be provided to the reaction mixture as a metalate anion or in a form which is converted to the desired metalate anion by subsequent chemical reaction. Hence, halide, sulfide, or the like, metal-containing compounds may be employed as the precursor to the desired metalate anion. Some of these precursor compounds may be converted to metalates during the hydrolysis reaction.

The metalate may be used in the salt form or may be introduced into the reaction system on a support, such as on a carrier such as silica, alumina, molecular sieves, zeolites, clay, and the like. When the process is carried out, the metalate is generally in a dissolved, mixed, suspended, or deposited form in a fixed bed in a liquid phase. The metalate may be provided to the reaction system by mixing it with alkylene oxide being introduced into the reaction system, it may be introduced by means of a separate inlet to the reaction system, or it may be retained in the reaction zone as an immiscible organic phase or solid phase. When the metalate-containing adjuvant is water-soluble, replenishing the reaction zone is desired. The exact means of introduction of the metalate is not critical, and frequently the metalate is provided at the beginning of the reaction and/or is continuously or intermittently added at a fixed rate during the reaction.

Formation of Alkylene Glycols

As stated above, alkylene glycols can be prepared from the corresponding alkylene oxide by direct reaction with water; however, the alkylene glycol formed can react with alkylene oxide to form dialkylene glycol and polyalkylene glycol side products. In accordance with the processes of this invention, this alkylene oxide and the metalate are believed to form an associated moiety which is then reacted with water to form the alkylene glycol. The associated moiety appears to have little if any, reactivity with alkylene oxide to form higher glycols. Thus, high selectivities to monoalkylene glycol can be achieved.

In processes of this invention, in a first stage alkylene oxide and metalate anion are contacted in a liquid medium under conditions sufficient to associate at least a portion of the alkylene oxide with metalate anion. The portion of the alkylene oxide associated with the metalate can vary widely depending upon the type of process employed and the amount of dialkylene glycol and higher glycols that are sought to be produced. For instance, if monoalkylene glycol that is substantially free from dialkylene glycol is sought, essentially all of the alkylene oxide may be associated with metalate anion, or any alkylene oxide which has not become associated with metalate anion may be removed from the liquid medium prior to its contact with water to form the alkylene oxide.

Very high yields of monoalkylene glycol can still be obtained when using insufficient metalate anion to become associated with the alkylene oxide on a stoichiometric basis. This phenomemon is believed to occur since in the alkylene glycol-forming stage, the associated moiety rapidly yields alkylene glycol and metalate anion when contacted with water. A regenerated metalate anion is thus available to enhance the selectivity of the reaction of alkylene oxide and water to the monoalkylene glycol.

The amount of metalate anion to be provided will also depend on the relative reactivity of the metalate with alkylene oxide as compared to that of water with alkylene oxide under the conditions of the alkylene glycol-forming stage. For example, high selectivities to monoalkylene glycols can be obtained using the active vanadates, molybdates and tungstates, even though significantly less metalate anion is provided than that required to react with the alkylene oxide on a stoichiometric basis to form the associated moiety. This occurs because of the relative activity of these metalates with the alkylene oxide.

In general, the molar ratio of alkylene oxide to metalate anion provided in the associated moiety-forming stage is in the range of about 20:1 to 1:20, say, about 5:1 to 0.5:1, and most preferably about 3:1 to 0.9:1. With metalate anions having more than one reactive site for association with alkylene oxide such as some molybdates and tungstates, the amount of metalate anions may be decreased accordingly. In some instances, it may be desired to provide sufficient amounts of metalate anion such that essentially all of the alkylene oxide becomes associated with metalate anion during the associated moiety-forming stage. In other instances, to provide processing advantages as described above or to minimize the metalate anion requirements, the amount of metalate anion provided may range from about 5 to 90 or 95 percent of that required for reaction on a stoichiometric basis. Hence, the product from the associated moiety forming stage may comprise about 5 to 90 mole percent of the alkylene oxide fed to that stage in unassociated form.

The liquid medium may be provided by the alkylene oxide and metalate-containing component, or a solvent in which the alkylene oxide is dissolved may be employed. Because the association is exothermic, it is generally preferred to employ a solvent for purposes of dissipating heat and thereby prevent high temperatures from occurring. Usually the solvent is provided in amounts of up to 40 or more times the weight of the alkylene oxide, e.g., the weight ratio of solvent to alkylene oxide is between about 30:1 to 1:30, and sometimes between about 20:1 to 1:5.

The solvent is preferably non-reactive with alkylene oxide and the metalate compound; however, in some instances it may be desirable to use interactive solvents such as 1,2-dimethoxyethane. Generally the alkylene oxide is miscible in all proportions under reaction conditions with the solvent, but processes of this invention may be attractive even though the solvent and alkylene oxide are substantially immiscible.

Organic solvents, particularly those which are immiscible in water, are desirable since the removal of a water-containing phase in the product from the glycol-forming stage may be easily effected by phase separation. Exemplary of liquid solvents are alkyl, cycloalkyl and aromatic-containing solvents, especially halogenated alkyl, cycloalkyls and aromatics, such as cyclopentane, cyclohexane, methylcyclohexane, cycloheptane, benzene, toluene, xylene, naphthene, dichloromethane, 1,1,2-trichloroethane, silicone oils, mineral oils, and the like. While advantages exist when using a substantially water-insoluble solvent, water-miscible solvents can also be used such as acetone, dimethyl sulfoxide, and the like. Not all the above solvents will be suitable for processes of this invention.

The metalate-containing material and/or the associated moiety may be in a substantially solid or liquid state under the conditions of the associated moiety-forming stage. When liquid, often a solvent is used. Generally, the solvent is substantially water-immiscible and is a solvent for the metalate in which the metalate-containing material is preferentially soluble as compared to water, e.g., the metalate-containing material is an organometalate with sufficient carbon atoms such that the organometalate is preferentially soluble in an organic solvent as compared to water at 25° C. Usually, at 25° C. the organometalate is soluble in the solvent in an amount of at least about 50 grams per liter. Sometimes the organometalate is at least five times as soluble in toluene as in water at 25° C. Hence, the recovery of the metalate anion after the glycol-forming stage is facilitated.

A water-immiscible phase may be denser or less dense than water. Often, the density of the water-immiscible phase is sufficiently different from that of, say, an aqueous alkylene glycol-containing phase formed in the glycol-forming stage to facilitate phase separation, e.g., the densities may differ by at least about 0.05, say, at least about 0.1, gram per milliliter under the conditions of the glycol-forming stage.

The associated moiety-forming stage has a substantial absence of polyglycol-forming amounts of water. Since the presence of water can result in the formation of dealkylene glycol which can compete with the metalate anion for reaction with alkylene oxide, the amount of water present is insufficient to result in appreciable amounts of dialkylene glycol and polyalkylene glycol being formed. Often less than 1 percent, preferably less than 0.5 percent, of the alkylene oxide is converted to dialkylene glycol or polyalkylene glycol in the associated moiety-forming stage. The amount of water which can be tolerated will depend upon many things including the reactivity of the metalate anion with the alkylene oxide, the mole ratio of alkylene oxide to metalate anion and the relative concentrations of the alkylene oxide and water. Hence, in some instances water may comprise a substantial portion of the reaction menstruum. Usually the mole ratio of water to alkylene oxide is less than about 0.5:1, say, less than about 0.1:1. Preferably, the liquid medium contains less than about 5 weight percent and most preferably less than about 0.5 percent water during the contacting step between alkylene oxide and metalate anion. Sometimes the liquid medium is substantially free from water; however, in other instances some water may be present to enhance the stability of the metalate anion, e.g., at least about 0.001, say, at least about 0.01, weight percent of the liquid medium comprises water.

The formation of the associated moiety is conducted under conditions of temperature and pressure sufficient for the reaction and to maintain the liquid phase. The temperature, however, should not be so great that the metalate-containing compound and the associated moiety are unduly adversely affected. Often, the reaction is carried out at temperatures between about 20° C. and about 220° C. or 250° C., say, between about 50° C. and 200° C., and sometimes between about 80° C. an 180° C. In some cases the metalate anion may be subject to reduction at elevated temperatures, particularly in the absence of water, and hence lower temperatures, e.g., below about 140° or 150° C. are preferred. When the associated moiety-forming stage involves the presence of water and a relatively active metalate anion such as vanadate, molybdate or tungstate, lower temperatures, e.g., in the range of about 35° C. to 120° C. may sometimes be preferred to suppress polyglycol-forming reactions.

The associated moiety-forming processes may be conducted at subatmospheric, atmospheric or above atmospheric pressure. However, often pressures are employed which are sufficient to maintain the associated moiety in the liquid phase. For purposes of convenience, the reaction is typically conducted at pressures greater than ambient, e.g., between about 0.1 and 1,000 kilograms per square centimeter gauge and preferably between about 2 and 100 kilograms per square centimeter gauge.

The alkylene oxide may be a gas under the conditions of the reaction and may be introduced into the liquid medium as a fine dispersion of gas bubbles, but most frequently, the pressure is sufficient to maintain the alkylene oxide in the liquid phase.

The formation of the associated moiety may be conducted in the presence of a gas, which is preferably inert. Gases which may be employed include air, carbon dioxide, nitrogen, argon and the like. Carbon dioxide is often present by the very nature of the process and the source of the alkylene oxide (especially by partial oxidation of ethylene). Frequently, it is desired to maintain the mole ratio of carbon dioxide to alkylene oxide less than 0.1:1, particularly less than 0.05:1, unless it is desired to affect the pH of the reaction menstruum.

Frequently, the associated moiety-forming reaction is conducted for a period of time sufficient to ensure that substantially all the metalate anion is reacted. However, it is apparent that the benefits of this invention can be obtained even though only a portion of the metalate anion is utilized. Usually, at least about 10 or 25 percent of the metalate anion (on a stoichiometric basis) is used to form the associated moiety in the associated moiety-forming zone. The amount of time required to accomplish the substantially complete reaction is determined by the other conditions employed including temperature, amount of reactants present, and the like. The reaction may be carried out for very short periods of time; e.g., fractions of a second, and if desired may be carried out for periods of up to hours, e.g. about 0.01 second to 5 hours, preferably about 1 second to 30 minutes.

The pH of the reaction menstruum is frequently maintained relatively neutral, e.g., between about 5 and 11, preferably about 6 to 10.5, and most often the pH is in the range of about 6 to 10. With some metalate anions, such as the vanadates, tungstates and molybdates, the pH of the medium can be determinative of the species present. For example, in strong bases the orthovanadate may predominate, but at neutral conditions metavanadate may exist. In another example, more acidic media promote the formation of polynuclear molybdates which often have less, if any, activity towards forming the associated moiety.

The pH may be maintained within the desired range by the addition of acid or base, or the addition of buffers, as is well known in the art. However, the presence and nature of salts should be considered since the cation may displace the cation for the metalate anion. Mechanisms which have been proposed for maintaining the desired pH in other types of hydrolysis processes include the addition of carbon dioxide or inorganic acids or organic acids such as sulfuric acid, hydrochloric acid and acetic acid. The agents for maintaining the pH value of the reaction menstruum may be added in any convenient manner such as during the reaction, e.g., by purging with carbon dioxide, or by addition to one or more of the reactants prior to introducing the reactants into the reactor.

The maintenance of the pH within the desired ranges can also have a secondary effect of enhancing the stability of the metalate anion.

The associated moiety formed by the metalate anion and alkylene oxide is then contacted with water under conditions sufficient to form alkylene glycol in an alkylene glycol-forming stage. The water may be provided as the liquid or as steam. The effluent from the associated moiety-forming stage may be directly processed to separate alkylene glycols from water or the effluent may be treated, e.g., by the separation of unassociated alkylene oxide.

Preferably, the amount of water employed in the glycol-forming stage is at least sufficient on a stoichiometric basis to react with the alkylene oxide values in the feed to that stage, which alkylene oxide values are equivalent to the sum of the alkylene oxide associated with the metalate anion and the unreacted alkylene oxide. Thus, the mole ratio of water or steam to total alkylene oxide values may be about 1:1 to 50:1. The associated moiety may provide a separate phase and may be continuously passed through an aqueous phase, or alternatively, steam or water may be passed through it. Hence, the mole ratio of water or steam to alkylene oxide values at a given section in the reaction menstruum may be greater or lesser than the foregoing mole ratios which are based on the net reactants provided to the reaction zone. When employing steam as the source of water for the liberation of alkylene glycol, little, if any, liquid water will be present in the alkylene glycol product and need to be separated from the product, e.g., by evaporation. Thus, higher ratios of steam to alkylene oxide values may be advantageous, for instance, mole ratios of about 5:1 to 40:1. On the other hand, when water is employed in amounts greater than that required on a stoichiometric basis to react with the alkylene oxide values, it must be removed from the alkylene glycol product. Therefore from the standpoint of energy efficiency, lower ratios of water to total alkylene oxide values are desirable, for instance, mole ratios of about 1:1 to 5:1. In general the ratio of water to total alkylene oxide values can be close to the stoichiometrically determined ratios without unduly sacrificing selectivity to the monoalkylene glycol product. Moreover, since the formation of the alkylene glycol from the associated moiety is not as exothermic as is the reaction between alkylene oxide and water, excess amounts of water need not be present for purposes of heat dissipation.

If desired, the glycol-forming stage may be conducted in the presence of a solvent. The solvent may be the same or different than that used in the associated moiety-forming stage, and adjuvants such as interactive solvents, pH modifiers, and the like, may be added to the menstruum of the glycol forming stage. Suitable solvents and interactive solvents include many of those set forth above for the associated moiety-forming stage. Frequently, when a water-immiscible solvent is used, the alkylene glycol product is preferentially soluble in water as compared to the solvent (e.g., at a reference condition of 25° C.) so that the recovery of the solvent is facilitated, e.g., by phase separation. The amount of solvent used may be the same or different from that used in the associated moiety-forming stage. In any event, when a solvent is employed the weight ratio of solvent to total alkylene oxide values passed to the glycol-forming stage is between about 50:1 to 1:50, e.g., about 30:1 to 1:30, and sometimes between about 20:1 to 1:5.

The temperature and pressure employed in the glycol-forming stage may be the same or different than those used in the associated moiety-forming stage. The reaction to form glycol sometimes proceeds even at low temperatures. Hence considerable flexibility exists in selecting temperatures for use in the glycol-forming stage. For instance, temperatures can be employed that are sufficiently low that the reaction between alkylene glycol and any unreacted alkylene oxide is inhibited or slowed to the extent that little, if any, dialkylene glycol or polyalkylene glycol can be formed. On the other hand, high temperatures, but below those that unduly adversely affect the metalate-containing material and/or the alkylene oxide and alkylene glycol, can be used. Frequently, the temperature is between about 20° C. and 220° C. or 250° C., say, about 30° C. to 200° C., and most often about 80° C. to 180° C.

The pressure is sufficient under the conditions in the glycol-forming zone to maintain the associated moiety and the metalate-containing compound in a non-gaseous state. The pressure is usually sufficient to maintain the alkylene glycol in the liquid phase as well as any solvent. In most instances, water is provided as a liquid and is maintained in the liquid phase in the glycol-forming stage. The pressure is typically greater than ambient, e.g., between about 0.1 and 1,000, preferably 2 and 100, kilograms per square centimeter gauge.

The reaction between water and the alkylene oxide values (as associated moiety and alkylene oxide) is generally conducted for a time sufficient to ensure that all the alkylene oxide values are reacted. Often the reaction is conducted for a very short period of time, e.g., fractions of a second, say about 1 second to about 30 minutes; however, longer periods of time, for instance five or more hours, can also be used.

The pH of the liquid medium in the glycol-forming stage is typically maintained relatively neutral, e.g., between about 5 and 11, preferably about 6 to 10.5, and most often about 6 to 10. As discussed above in connection with the associated metalate-forming stage, any adjuvant used to adjust the pH should be selected on the basis of avoiding adverse effects to the metalate-containing material.

The glycol-forming reaction may be conducted in the presence of a gas, which is preferably inert and may be the same or different gas than that which may have been present in the associated moiety-forming stage. Gases which may be suitable include air, carbon dioxide, nitrogen, argon and the like. Carbon dioxide is often present and generally the mole ratio of carbon dioxide to total alkylene oxide values is less than 0.1:1 unless the carbon dioxide is provided to affect the pH of the reaction medium. Carbon dioxide can be used in certain amounts to enhance the selectivity provided by vanadate anion such as disclosed in U.S. patent application Ser. No. 594,265, filed on even date herewith, of B. T. Keen, herein incorporated by reference.

The process may be conducted in any convenient manner. For example, the process may be conducted in two vessels, the first for forming the associated moiety and the second for forming the alkylene glycol. It is also possible to conduct the process in a single vessel having several zones; in the first portion of the vessel the metalate anion and alkylene oxide are contacted and in a subsequent portion, water or steam is introduced. The vessels may be provided with means to promote the contact between the reactants. For example, agitators, packing, trays and other devices for promoting liquid-liquid or gas-liquid contact, as the case may be, may be employed.

In some processes of this invention, the metalate anion-containing material remains in a non-aqueous phase, e.g., the metalate anion-containing material comprises a solid phase or a water-immiscible phase. In these aspects of the invention, it is sometimes desirable to add small quantities of a more soluble metalate anion-containing material to the reaction menstruum during the process to assist in stabilizing the metalate anion-containing material in the non-aqueous phase. The added metalate anion is often provided in amounts less than about 1000 ppm by weight, say, about 5 to 250 ppm by weight, such as described in U.S. patent application Ser. No. 594,267, filed on even date herewith, of B. T. Keen, herein incorporated by reference.

It is desired to separate the alkylene glycol product from the reaction medium from the glycol-forming stage. Preferably, the metalate-containing material is also separated and returned to the associated moiety-forming stage to provide a commercially viable, continuous process. The separation techniques are advantageously selected with consideration to providing an integrated process for making alkylene glycols from alkylene oxides. For example, the separation may be effected by phase separation when a water-immiscible solvent is employed in the associated moiety-forming stage and/or the glycol-forming stage and the solvent selected is a better solvent for the metalate-containing compound than water but is a worse solvent than water for alkylene glycol. The alkylene glycol-rich aqueous phase can be refined to recover high purity monoalkylene glycol, for instance, by the use of multiple effect evaporators to remove water and distillation, e.g., vacuum distillation, to refine the monoalkylene glycol from higher glycol impurities and other impurities. The metalate anion-rich solvent phase can be recycled to the associated moiety-forming stage.

It is not necessary, however, to use a two liquid phase reaction system to obtain the benefits of the invention. For instance, with solid metalate-containing materials, the alkylene glycol can be separated as the liquid phase after, e.g., settling or filtration.

The metalate-containing material can be extracted from the alkylene glycol-containing phase by contact with an immiscible liquid in which the metalate-containing material is preferentially soluble. For further discussion see U.S. patent application Ser. No. 594,266, filed on even date herewith, of B. T. Keen, et al., herein incorporated by reference. Alternatively, the alkylene glycol containing medium may be contacted with, for instance, an anion exchange resin such as a chloride-loaded DOWEX TM MSA-1 resin available from the Dow Chemical Company to recover the metalate anion. This resin can be separated and regenerated with the metalate anion being returned to the associated moiety-forming stage. The alkylene glycol can be recovered and refined in a suitable manner. See for further discussion U.S. patent application Ser. No. 594,269, filed on even date herewith, of J. A. Collier, herein incorporated by reference. It is also possible to recover the metalate anion-containing material by distillation (e.g., evaporation or fractional distillation) from the alkylene glycols. When employing higher temperature separation processes, e.g., above about 100° or 120° C., the provision of small amounts of water enhances the stability of many metalate anions.

The following examples are provided to assist in the understanding of the invention and are not in limitation thereof. All percentages and parts of solids are by weight and all percentages and parts of liquids and gases are by volume unless otherwise indicated.

The analyses of the reaction products were conducted at temperature programmed gas chromatography using 10 ft×⅛" stainless steel column packed with Chromosorb 101 TM (60/80 mesh available from Supelco, Inc., Bellefonte, Pa.). Sample injections (2–3 microliters) were made from a sample of 1.5 to 2.0 grams of hydrolysis product to which had been added 0.12 to 0.15 gram of 2-ethyl-1,3-hexanediol as internal standard. In Examples 8 to 11, the analysis included adding about 50 microliters of the sample to 1.0 milliliter of Regisil TM (BSTFA) (N,N-bistrimethylsilyl trifluoroacetamide), available from the Regis Chemical Company, Morton Grove, Ill., in a serum vial and mixed for at least about 12 hours.

Selectivities are defined as $[G/(M+D+T)]$ times 100% where G is the weight of the glycol in question, M is the weight of monoalkylene glycol, D is the weight of dialkylene glycol and T is the weight of trialkylene glycol.

EXAMPLE 1

A 100 milliliter, round bottom, glass flask was charged with about 3.01 grams of bis[bis(triphenylphosphine)iminium]molybdate and about 14.35 grams of ethylene oxide were condensed into the flask. Thereafter, 10 milliliters of dichloromethane (0° C.) were added. The mixture was allowed to stand for about three hours. The solvent and ethylene oxide were then stripped under vacuum (about 1 to 2 millibars absolute). Approximately 10 milliliters of 1,1,2-trichloroethane and 0.18 grams of distilled water were added to the residue and refluxed at ambient pressure for about 2 hours and 20 minutes under a dry ice/acetone condenser. The condenser was washed with 1,1,2-trichloroethane and then water. The aqueous layer was separated and was analyzed to contain monoethylene glycol. No diethylene glycol or triethylene glycol was detected.

EXAMPLE 2

To a stirred, 50 milliliter, roundbottom glass flask equipped with a condenser were charged 4.9 grams of bis(tetra-n-hexylammonium)molybdate and 20 milliliters of toluene (distilled from calcium hydride). The resulting mixture was chilled to about 0.5° C. in ice water and about 9.52 grams of ethylene oxide (about 0° C.) were added. The mixture was refluxed at ambient pressure for about 5 hours. The volatiles were stripped under vacuum (about 1 to 2 millibars absolute) and a viscous greem mass of material was obtained. To this material was added 20 milliliters of toluene and about 0.107 milliliters of water and the mixture was heated to reflux for two hours at ambient pressure. The initial green color of the solution changed to a light brown. The condenser was washed with about 2 milliliters of water and then with 5 milliliters of toluene. The volatiles were distilled from the flask, recovering ethylene glycol at a bottom temperature of about 95° C. to 98° C. under a pressure of about 0.5 millibars absolute.

Table I, which follows, provides a further expansion of the principles illustrated in the preceding examples.

quots of one of the stock solutions A to D and one of the stock solutions E and F were introduced using suitably sized syringes into a microreactor (both predried), the microreactor sealed and introduced into a constant temperature bath at 60° C. for two hours under a reciprocating motion. The microreactors were then withdrawn, cooled to about room temperature over night, opened, water charged, resealed and again heated in the bath at 60° C. for one hour. Thereafter, the microreactors were cooled and the contents analyzed. The details are provided in Table II.

TABLE II

| Example | Stock Solution Identity | Stock Solution Amount (ml) | Stock Solution Identity | Stock Solution Amount (ml) | Water ml | MEG Selectivity % |
|---|---|---|---|---|---|---|
| 8 | A | 5.0 | E | 1.0 | 0.072 | 98.3% |
| 9 | B | 5.0 | F | 0.66 | 0.036 | 100% |
| 10 | C | 5.0 | F | 0.66 | 0.14 | 100% |
| 11 | D | 4.0 | F | 1.6 | 0.15 | * |

*incomplete conversion of ethylene oxide

It is claimed:

1. A process for making alkylene glycols comprising contacting alkylene oxide with a selectivity enhancing, dissociatable, metalate anion-containing material under conditions sufficient to associate at least a portion of the alkylene oxide with the metalate anion, said contacting being in the substantial absence of polyglycol forming amounts of water; and then contacting with water the metalate anion associated with alkylene oxide under conditions sufficient to form alkylene glycol.

2. The process of claim 1 wherein the metalate anion has the formula $[(A)_qM(O)]^a$ where M is a polyvalent

TABLE I

| Example No. | Metalate | Alkylene Oxide | Mole Ratio/ Metalate:Oxide | Solvent | Mole Ratio Water/Total Alkylene Use | Predominant Product |
|---|---|---|---|---|---|---|
| 3 | tetra-n-hexylammonium vanadate (pH 10) | ethylene oxide | 1:2 | dichloromethane | 5:1 | monoethylene glycol |
| 4 | bis[bis(triphenyl-phosphine)iminium]-tungstate | ethylene oxide | 1:1 | toluene | 2:1 | monoethylene glycol |
| 5 | bis(tetra-n-propyl-ammonium) molybdate | ethylene glycol | 0.1:2 | benzene | 2:1 | monoethylene glycol |
| 6 | bis[bis(triphenyl-phosphine)iminium]-molybdate | 1,2-epoxy butane | 0.5:1 | dichloromethane | 10:1 | 1,2-dihydroxybutane |
| 7 | tetra-n-hexylammonium rhenate | ethylene oxide | 1:1 | toluene | 2:1 | monoethylene glycol |

EXAMPLES 8 TO 11

The following stock solutions were prepared:

Solution A: 2.0 grams BTHAM* and 5.0 grams dichloromethane

Solution B: 2.0 grams BTHAM and 5.0 grams tetrahydrofuran

Solution C: 2.0 grams BTHAM and 5.0 grams tetrahydrofuran

Solution D: 0.4 grams BTHAM and 4.0 grams tetrahydrofuran

Solution E:** 4.4 grams ethylene oxide and 46 milliliters dichloromethane

Solution F:** 4.4 grams ethylene oxide and 46 milliliters tetrahydrofuran

*BTHAM is (bis(tetrahexyl)ammonium)molybdate
**chilled (about 0°-5° C.)

The processes were conducted using stainless steel microreactors having a length of about 9 centimeters and an outside diameter of about 1.3 centimeters. Alimetal having a functional positive oxidation state; A represents one or more substituents to fill the remaining valencies (q) of M, and a is the negative charge of the anion.

3. The process of claim 1 wherein the metalate anion is selected from the group consisting of molybdate, tungstate, metavanadate, pyrovanadate and hydrogen pyrovanadate.

4. The process of claim 3 wherein the alkylene oxide has the formula $$R^1-\underset{R^2}{\overset{}{C}}\overset{O}{\overbrace{\phantom{XXXX}}}\underset{R^3}{\overset{}{C}}-R^4$$

wherein each of $R^1$, $R^2$, $R^3$ and $R^4$ are the same or different and are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbons.

5. The process of claim 4 wherein the alkylene oxide is ethylene oxide.

6. The process of claim 1 wherein the mole ratio of alkylene oxide to metalate anion is between about 20:1 to 1:20.

7. The process of claim 5 wherein the mole ratio of ethylene oxide to metalate anion is between about 20:1 to 1:20.

8. The process of claim 7 wherein at least a portion of the unassociated ethylene oxide is removed from the liquid medium prior to the contacting of water with the metalate anion associated with ethylene oxide.

9. The process of claim 6 wherein about 5 to about 90 percent of the alkylene oxide is unassociated with the metalate and is passed with the liquid medium for contact with water.

10. The process of claim 5 wherein the liquid medium contains less than about 5 weight percent water during the contacting step between ethylene oxide and metalate anion.

11. The process of claim 10 wherein the liquid medium contains less than about 0.5 weight percent water during the contacting step between ethylene oxide and metalate anion.

12. The process of claim 6 wherein the liquid medium comprises an organic solvent for the metalate.

13. The process of claim 12 wherein the weight ratio of solvent to alkylene oxide is between about 20:1 to 1:5.

14. The process of claim 12 wherein the solvent is substantially immiscible with water.

15. The process of claim 14 wherein the solvent comprises at least one member selected from the group consisting of benzene, toluene, xylene, dichloromethane and 1,1,2-trichloroethane.

16. The process of claim 14 wherein the metalate anion is provided with at least one organo-containing cation.

17. The process of claim 16 wherein the organo-containing carbon has sufficient carbon atoms to render the metalate preferentially soluble in the organic solvent as compared to water at 25° C.

18. The process of claim 17 wherein the organic-containing cation is represented by the formula $$[(R^0)_m Y_n]^{x+}$$

wherein Y is a polyvalent element which is an ionic charge carrying center; $R^0$ is hydrogen or hydrocarbyl-containing substituent with the proviso that Y has at least one $R^0$ which contains a hydrocarbyl substituent; m is the average number of electron pairs shared by Y with the total $R^0$ groups; and n is the number of charge carrying centers, wherein m, n and x are related by the equation x=n(V-m) in which V is the average functional oxidation state of Y wherein each electron pair used by each Y in bonding to R is given the value of 1 and the formal oxidation state of Y is the sum of the electron pairs bonding to $R^0$ and x/n, and x is an integer of 1 or 2.

19. The process of claim 18 wherein the organic-containing cation comprises ammonium cation.

20. The process of claim 19 wherein the ammonium cation comprises tetraalkyl ammonium cation.

21. The process of claim 18 wherein the organic-containing cation comprises quaternary phosphonium cation.

22. The process of claim 18 wherein the organic-containing cation comprises bis(trisubstituted-phosphine)iminium cation.

* * * * *